(12) United States Patent
Ikeda

(10) Patent No.: US 10,959,604 B2
(45) Date of Patent: Mar. 30, 2021

(54) FLEXIBLE TUBE INSERTION APPARATUS

(71) Applicant: OLYMPUS CORPORATION, Tokyo (JP)

(72) Inventor: Yuichi Ikeda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 362 days.

(21) Appl. No.: 16/159,822

(22) Filed: Oct. 15, 2018

(65) Prior Publication Data

US 2019/0046012 A1    Feb. 14, 2019

Related U.S. Application Data

(63) Continuation of application No. PCT/JP2016/062808, filed on Apr. 22, 2016.

(51) Int. Cl.
*A61B 1/00* (2006.01)
*A61B 1/06* (2006.01)
(Continued)

(52) U.S. Cl.
CPC ...... *A61B 1/00078* (2013.01); *A61B 1/00006* (2013.01); *A61B 1/00066* (2013.01);
(Continued)

(58) Field of Classification Search
CPC ............ A61B 1/00006; A61B 1/00066; A61B 1/00078; A61B 1/00163; A61B 1/0051;
(Continued)

(56) References Cited

U.S. PATENT DOCUMENTS 4,930,494 A * 6/1990 Takehana ........... A61B 1/00147
600/145
5,482,029 A * 1/1996 Sekiguchi .......... A61B 1/00039
600/109
(Continued)

FOREIGN PATENT DOCUMENTS

JP     2015-002861 A    1/2015
JP     2015-016365 A    1/2015
(Continued)

OTHER PUBLICATIONS

International Search Report dated Jul. 26, 2016 issued in PCT/JP2016/062808.
(Continued)

*Primary Examiner* — Quynh-Nhu H. Vu
(74) *Attorney, Agent, or Firm* — Scully, Scott, Murphy & Presser, P.C.

(57) ABSTRACT

A flexible tube insertion apparatus includes a flexible tube to be inserted into an insertion target body, a variable stiffness portion that changes a bending stiffness of the flexible tube, a state detection sensor that detects state information of the flexible tube. The apparatus also includes a shape calculator that calculates shape information regarding a shape of the flexible tube based on the state information, an external force calculator that calculates external force information including magnitude of an external force received by the flexible tube based on the state information, and a stiffness controller that controls the variable stiffness portion in accordance with the shape information so that the magnitude of the external force received by the flexible tube becomes smaller than a reference value.

7 Claims, 3 Drawing Sheets

(51) Int. Cl.
*A61M 25/00* (2006.01)
*A61B 1/005* (2006.01)
*A61B 1/05* (2006.01)

(52) U.S. Cl.
CPC ......... *A61B 1/0676* (2013.01); *A61M 25/005* (2013.01); *A61M 25/0054* (2013.01); *A61B 1/0051* (2013.01); *A61B 1/00163* (2013.01); *A61B 1/05* (2013.01); *A61M 25/0012* (2013.01); *A61M 2025/0058* (2013.01)

(58) Field of Classification Search
CPC ............... A61B 1/05; A61B 1/0676; A61M 2025/0058; A61M 25/0012; A61M 25/005; A61M 25/0053; A61M 25/0054
See application file for complete search history.

(56) References Cited

U.S. PATENT DOCUMENTS

| | | | | |
|---|---|---|---|---|
| 8,827,894 B2* | 9/2014 | Belson | ..................... | A61B 1/31 600/114 |
| 10,349,819 B2* | 7/2019 | Ikeda | ....................... | A61B 1/00 |
| 2004/0193014 A1* | 9/2004 | Miyagi | .............. | A61B 1/00039 600/146 |
| 2007/0149852 A1* | 6/2007 | Noguchi | .............. | A61B 1/0051 600/144 |
| 2011/0237889 A1* | 9/2011 | Tanaka | ............... | A61B 1/00039 600/118 |
| 2013/0169272 A1* | 7/2013 | Eichler | ................... | A61B 5/062 324/253 |
| 2014/0230562 A1* | 8/2014 | Yamamoto | ............... | G01N 3/20 73/800 |
| 2017/0079508 A1* | 3/2017 | Ikeda | .................. | A61B 1/0055 |

FOREIGN PATENT DOCUMENTS

| | | |
|---|---|---|
| JP | 2016-007434 A | 1/2016 |
| WO | WO 2015/083473 A1 | 6/2015 |

OTHER PUBLICATIONS

English translation of International Preliminary Report on Patentability dated Nov. 1, 2018 together with the Written Opinion received in related International Application No. PCT/JP2016/062808.

* cited by examiner

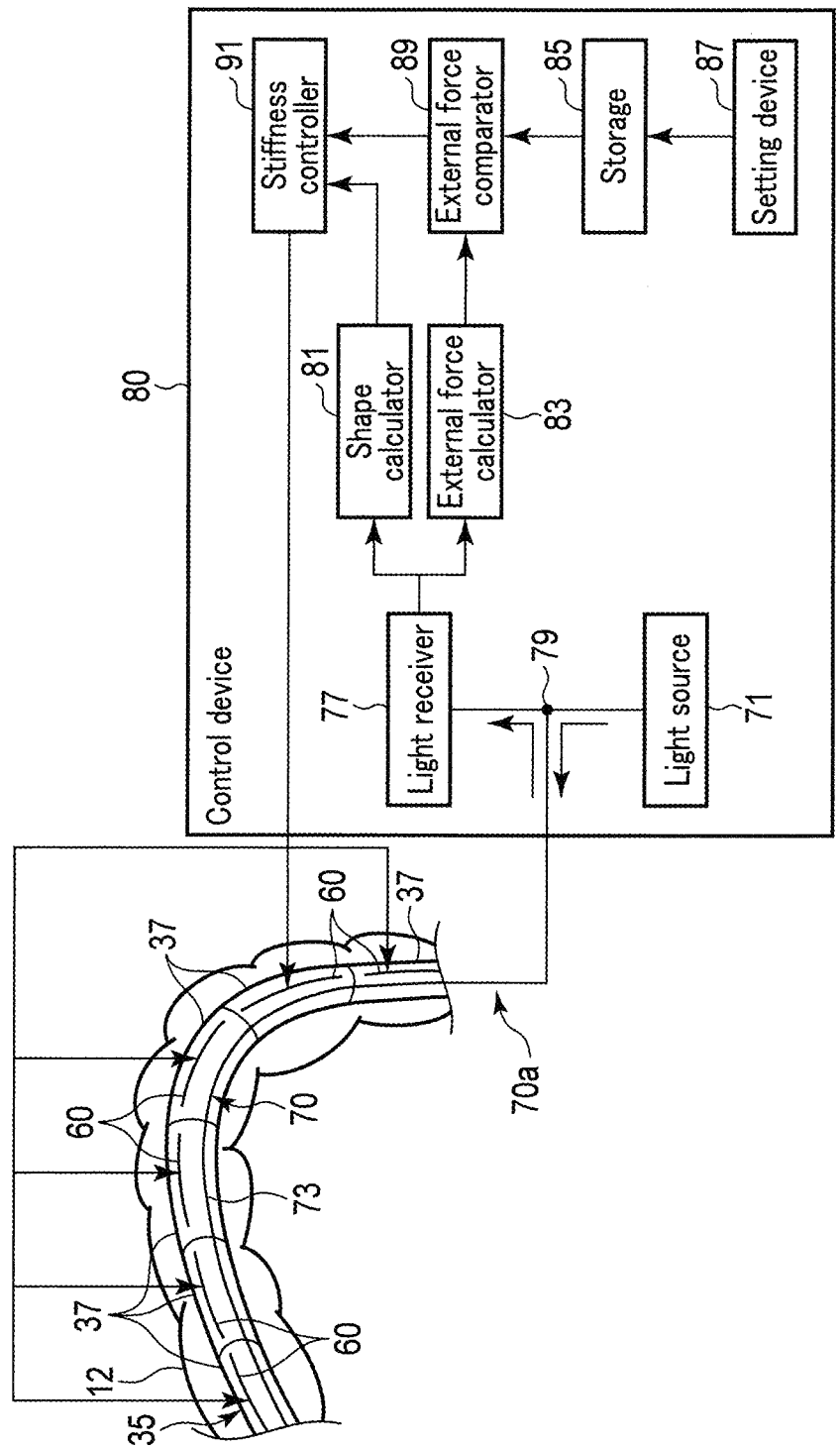
F I G. 2

FLEXIBLE TUBE INSERTION APPARATUS

CROSS-REFERENCE TO RELATED APPLICATIONS

This application is a Continuation Application of PCT Application No. PCT/JP2016/062808, filed Apr. 22, 2016, the entire contents of which are incorporated herein by reference.

BACKGROUND OF THE INVENTION

1. Field of the Invention

The present invention relates to a flexible tube insertion apparatus that inserts a flexible tube into a tract section of an insertion target body.

2. Description of the Related Art

A flexible tube of an insertion section of an endoscope apparatus disclosed in, for example, Jpn. Pat. Appln. KOKAI Publication No. 2016-7434 is partitioned in segments aligned in a row along a central axis of the insertion section. The endoscope apparatus changes a bending stiffness of the flexible tube to a bending stiffness suitable for insertion by units of segments in accordance with the shape of the flexible tube calculated by a shape calculator. This allows insertability of the insertion section to improve when performing a push operation of the insertion section into a deep part of a tract section (for example, an intestine tract of a large intestine) of an insertion target body (for example, a large intestine).

A tube-like insertion apparatus disclosed in Jpn. Pat. Appln. KOKAI Publication No. 2015-16365, for example, provides an operator with control assistance information that is information necessary for insertion of an insertion section and that includes shape information regarding a shape of the insertion section and external force information regarding external force received by the insertion section. The operator is assisted on the insertion operation of the insertion section by the control assistance information.

BRIEF SUMMARY OF THE INVENTION

An aspect of a flexible tube insertion apparatus of the present invention includes a flexible tube that is to be inserted into an insertion target body, a variable stiffness portion that changes a bending stiffness of the flexible tube, a state detection sensor that detects state information including information of magnitude of bending of the flexible tube, a shape calculator that calculates shape information regarding a shape of the flexible tube based on the state information, an external force calculator that calculates external force information including magnitude of an external force received by the flexible tube based on the state information; and a stiffness controller that controls the variable stiffness portion in accordance with the shape information so that the magnitude of the external force received by the flexible tube becomes smaller than a predetermined external force reference value.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram explaining relationships among segments, a state detection sensor, a shape calculator, an external force calculator, a storage, a setting device, an external force comparator, a stiffness controller, and variable stiffness portions.

DETAILED DESCRIPTION OF THE INVENTION

In the following, an embodiment of the present invention will be explained in detail with reference to the figures. In some of the figures, illustrations of some members are omitted to obtain a clarified illustration.

Figure 1:
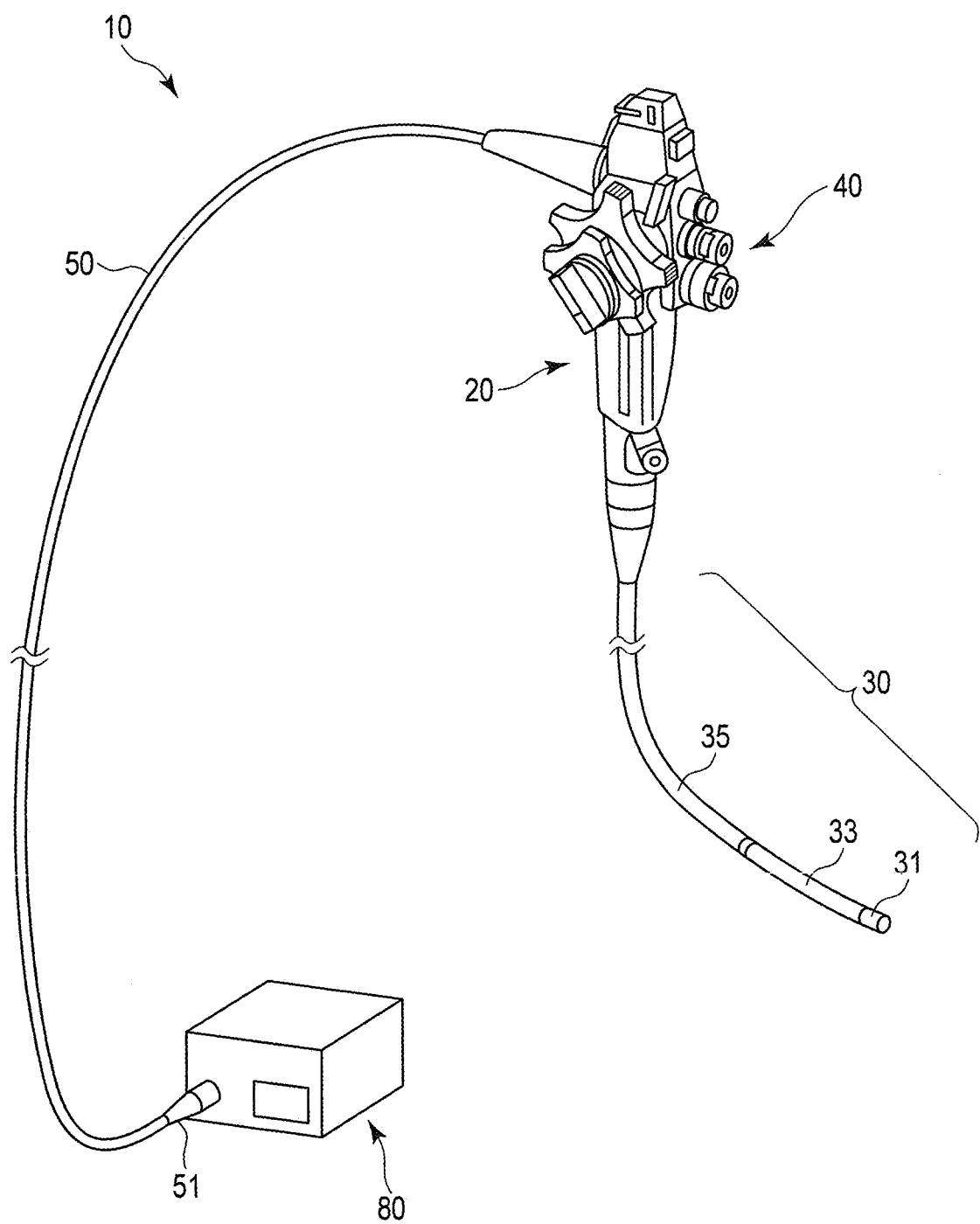
FIG. 1 is a schematic view of a flexible tube insertion apparatus according to an embodiment of a present invention.

As shown in FIG. 1, a flexible tube insertion apparatus (hereinafter referred to as an insertion apparatus 10) comprises an endoscope 20 and a control device 80 that controls the endoscope 20. The control device 80 functions, for example, as a stiffness control apparatus that controls a bending stiffness of a flexible tube 35 of an insertion section 30 that is arranged in the endoscope 20. Although not illustrated, the insertion apparatus 10 may also comprise a display device that displays an image imaged by the endoscope 20, and a light source device that emits light for the endoscope 20 to observe and image.

The endoscope 20 will be explained as, for example, a medical soft endoscope; however, the endoscope 20 is not limited to this. The endoscope 20 only has to include a soft insertion section 30 that is to be inserted in a tract section (for example, an intestine tract 12 of a large intestine (refer to FIG. 2)) of an insertion target body (for example, a patient), such as an industrial soft endoscope, a catheter, and a treatment device. The insertion section 30 only has to include a portion (for example, a flexible tube 35 explained later on) with flexibility that can be bent by external force. The endoscope 20 may be a direct-view type endoscope, or a side-view type endoscope. The insertion target body, for example, is not limited to a human, and may be an animal, or other structures. The tract section may be, for example, an industrial pipe.

The endoscope 20 comprises the insertion section 30, a control section 40 that is connected to a proximal end of the insertion section 30 and operates the endoscope 20, and a universal cord 50 that extends from a side surface of the control section 40. The universal cord 50 has a connector 51 that is attachable to and detachable from the control device 80.

The insertion section 30 is tubular, elongated, and flexible. The insertion section 30 moves back and forth inside the tract section with respect to the tract section. The insertion section 30 is bendable in accordance with a shape of the tract section. The insertion section 30 comprises, from its distal end to its proximal end, a distal hard section 31, a bendable section 33, and the flexible tube 35, in this order. The distal hard section 31 and the bendable section 33 are shorter than the flexible tube 35. Therefore, in the present embodiment, the distal hard section 31, the bendable section 33, and the distal end of the flexible tube 35 are regarded as the distal end of the insertion section 30. The flexible tube 35 has flexibility and is bent by external force.

As shown in FIG. 2, the flexible tube 35 of the insertion section 30 is segmented into segments 37 aligned in a row along a central axis of the insertion section 30. For example, the segments 37 are present over an entire length of the flexible tube 35. The bending stiffness of each segment 37 is independently changeable by the control of the control device 80. Accordingly, the bending stiffness of the flexible tube 35 is partially changeable by the bending stiffness of each segment 37 that is independently controlled by the control device 80. Each segment 37 may function as a virtual region that does not actually exist, or may function as a structure that actually exists. Each length of the segments 37 may be identical to or may differ from each other. For example, the length of a portion to be inserted into the insertion target body at the insertion section 30 depends on the insertion target body. Accordingly, the portion to be inserted may be considered as being segmented into segments 37, and a portion that is arranged outside the insertion target body and is not to be inserted into the insertion target body may be considered as being one segment 37.

The insertion apparatus 10 includes variable stiffness portions 60 that each have stiffness that is variable by the control of the control device 80, and that change the bending stiffness of the flexible tube 35 by the stiffness. In the present embodiment, the variable stiffness portions 60 vary the bending stiffness of the flexible tube 35 in the insertion section 30 by units of segments 37. Therefore, it is explained that, for example, each variable stiffness portion 60 is embedded in each segment 37, and the variable stiffness portions 60 are embedded over the entire length of the flexible tube 35. The variable stiffness portions 60 only have to be arranged on portions that are inserted in the tract section and that need to have the bending stiffness changed in the flexible tube 35. That is, the variable stiffness portions 60 may be embedded only in some of the segments 37.

Portions on which the variable stiffness portions 60 are provided may at least function as the segments 37. A variable stiffness portion 60 may be embedded over segments 37. The variable stiffness portions 60 may be aligned in a row, or in rows along a central axis of the insertion section 30. In a case where the variable stiffness portions 60 are aligned in rows, a set of variable stiffness portions 60 may be provided at the same position so that the variable stiffness portions 60 are adjacent to each other in a circumferential direction of the flexible tube 35 or so that the variable stiffness portions 60 are shifted along the central axis of the insertion section 30.

Although not shown, each variable stiffness portion 60 is configured by an actuator that comprises, for example, a coil pipe that is formed by a metal wire, and an electroactive polymer artificial muscle (hereinafter referred to as EPAM) encapsulated inside the coil pipe. The central axis of the coil pipe is coincide with or in parallel to the central axis of the insertion section 30. The coil pipe includes a pair of electrodes that is provided on the both ends of the coil pipe.

Electrodes of each variable stiffness portion 60 are connected to the control device 80 through signal cables that are embedded in the endoscope 20, respectively, and receive electric power from the control device 80. When a voltage is applied to the EPAM through the electrode, the EPAM attempts to expand and contract along the central axis of the coil pipe. However, the coil pipe restricts the expansion and contraction of the EPAM. In this manner, the stiffness of a variable stiffness portion 60 changes. The stiffness of the variable stiffness portion 60 increases as the applied voltage value increases. The stiffness of the variable stiffness portion 60 changes; the bending stiffness of the corresponding segment 37 also changes. The electric power is supplied independently to each pair of electrodes of the variable stiffness portions 60. Therefore, the stiffness of each variable stiffness portion 60 changes independently; the bending stiffness of each segment 37 also changes independently. In this manner, each variable stiffness portion 60 causes the bending stiffness of the corresponding segment 37 to change according to the stiffness change of the variable stiffness portion 60; the bending stiffness change of the segment 37 causes the bending stiffness of the flexible tube 35 to partially change.

The variable stiffness portion 60 may also use a shape-memory alloy instead of the EPAM.

The insertion apparatus 10 includes a state detection sensor 70 that detects state information of the flexible tube 35 regarding the state of the flexible tube 35. In the present embodiment, the state of the flexible tube 35 indicates a bending state of the flexible tube 35, for example, a bending quantity (magnitude of bending) of the flexible tube 35. The state of the flexible tube 35 may include a bending direction of the flexible tube 35.

As an example, the state detection sensor 70 includes a fiber sensor 70a that utilizes a loss of a light transmission quantity caused by bending an optical fiber 73. The fiber sensor 70a comprises a light source 71 that emits light, the optical fiber 73 that guides the light, a reflector (not shown) that reflects light so that the light guided by the optical fiber 73 travels backwards in the optical fiber 73, a light receiver 77 that receives the reflected light, and a light branching unit 79. The light source 71 includes, for example, an LED. The light source 71 is separate from a light source of the light source device that emits light for observation and imaging. The optical fiber 73 is embedded in the endoscope 20 and has flexibility. The optical fiber 73 has detection targets (not shown) that are mounted on the insertion section 30. The detection targets are arranged at positions that are different from each other along a longitudinal axial of the optical fiber 73. The detection targets only have to be arranged at portions where the bending stiffness of the flexible tube 35 is to be changed. Accordingly, in the present embodiment, suppose the detection targets are arranged on each segment 37 inside the flexible tube 35. The optical fiber 73 is arranged alongside the variable stiffness portions 60 in the flexible tube 35. The reflector is arranged at the distal end of the optical fiber 73, which is positioned at the distal end of the insertion section 30. The light receiver 77 may comprise, for example, an element for spectral dispersion such as a spectroscope or a color filter, and alight receiving element such as a photodiode. The light source 71, the light receiver 77, and the proximal end of the optical fiber 73 are optically connected to the light branching unit 79. The light branching unit 79 comprises, for example, an optical coupler or a half mirror. The light branching unit 79 guides the light emitted from the light source 71 to the optical fiber 73, and guides returned light reflected by the reflector and guided by the optical fiber 73 to the light receiver 77. That is, the light travels in the order of the light source 71, the light branching unit 79, the optical fiber 73, the reflector, the optical fiber 73, the light branching unit 79, and the light receiver 77. The light source 71, the light receiver 77, and the light branching unit 79 are, for example, mounted on the control device 80.

When the insertion section 30 is bent, the optical fiber 73 is bent in accordance with such bending. Accordingly, a part of light that propagates through the optical fiber 73 is emitted (leaks) outside through, for example, the detection targets that have sensitivity in different wavelengths from each other. The detection target changes optical characteristics of the optical fiber 73; such as the light transmission quantity of light of a predetermined wavelength. Therefore, when the optical fiber 73 is bent, the light transmission quantity of the optical fiber 73 changes in accordance with the bending quantity of the optical fiber 73. A light signal that includes information of the change in the light transmission quantity is received at the light receiver 77. The light receiver 77 outputs the light signal as state information of the flexible tube 35 to a shape calculator 81 and an external force calculator 83 explained later on, arranged in the control device 80.

One detection target may be arranged on one optical fiber 73; in which case optical fibers will be arranged. Furthermore, suppose detection targets are arranged at the same position or at nearby positions along the longitudinal axial of the optical fiber, and at positions different from each other in a circumferential direction about the longitudinal axis. In such case, the bending quantity and the bending direction can be detected by a combination of the detection results of the detection targets.

The state detection sensor 70 is not limited to comprising the fiber sensor 70a. The state detection sensor 70 may also comprise one of, for example, a strain sensor, an acceleration sensor, a gyro sensor, and an element such as a coil. The strain sensor detects, for example, a bending strain caused by an external force (pressure) that the flexible tube 35 receives externally (for example, from the tract section). The acceleration sensor detects accelerated velocity of the flexible tube 35. The gyro sensor detects angular velocity of the flexible tube 35. The element generates a magnetic field corresponding to the state of the flexible tube 35, such as the shape of the flexible tube 35.

The state detection sensor 70 constantly performs detection (operates) after a detection start instruction is input to the state detection sensor 70 from an input device (not shown). The timing of detection may be implemented every lapse of a certain time, which is not limited in particular. The input device is general equipment for input, which, for example, may be a keyboard, a pointing device such as a mouse, a tag reader, a button switch, a slider, or a dial. The input device is connected to the control device 80. The input device may be used to input various instructions for a user to operate the insertion apparatus 10.

The insertion apparatus 10 comprises the shape calculator 81, the external force calculator 83, a storage 85, a setting device 87, an external force comparator 89, and a stiffness controller 91. For example, the shape calculator 81, the external force calculator 83, the storage 85, the setting device 87, the external force comparator 89, and the stiffness controller 91 can be arranged in the control device 80.

The shape calculator 81, the external force calculator 83, the external force comparator 89, and the stiffness controller 91 are, for example, configured by a hardware circuit that includes ASIC, etc. The shape calculator 81, the external force calculator 83, the external force comparator 89, and the stiffness controller 91 may also be configured by a processor. In the case where the shape calculator 81, the external force calculator 83, the external force comparator 89, and the stiffness controller 91 are configured by a processor, a program code that causes the processor to function as the shape calculator 81, the external force calculator 83, the external force comparator 89, and the stiffness controller 91 by executing the processor has been stored in an internal memory or an external memory (not shown) that is accessible by the processor.

The shape calculator 81 calculates shape information regarding the shape of the flexible tube 35 along the central axis of the flexible tube 35 based on the state information. For example, the shape calculator 81 calculates the shape information of the flexible tube 35 from the relationship of characteristics between incoming light and outgoing light of the optical fiber 73. In detail, the shape calculator 81 calculates the shape information, specifically, the bending shape of the flexible tube 35 of a part that is actually bending, based on the state information output from the fiber sensor 70a. Therefore, the shape calculator 81 calculates the shape information of each segment 37 based on the state information. The shape calculator 81 calculates the shape information of the flexible tube 35 by joining the shape information of each segment. The shape calculator 81 outputs the calculated shape information to the stiffness controller 91.

The external force calculator 83 calculates external force information that includes the magnitude of the external force (pressure) received by the flexible tube 35 based on the state information. The external force information may also include the direction of the external force. For example, the external force calculator 83 calculates the external force information from the relationship of characteristics between incoming light and outgoing light of the optical fiber 73. In detail, the external force calculator 83 calculates the external force information regarding, for example, the external force that the flexible tube 35 receives from the large intestine wall, based on the state information output from the light receiver 77. The external force calculator 83 calculates the external force information in each segment 37 based on the state information. The external force referred to herein indicates, for example, a force that is applied to the segment 37 vertically with respect to the central axis of the segment 37 (central axis of the insertion section 30). The external force calculator 83 outputs the calculated external force information to the external force comparator 89.

In a state where the detection result of the state detection sensor 70 is input, the shape calculator 81 and the external force calculator 83 constantly perform calculation (operates) after a calculation start instruction is input to the shape calculator 81 and the external force calculator 83 from the input device. The timing of calculation may be implemented every lapse of a certain time, which is not limited in particular.

The storage 85 stores a reference value (hereinafter referred to as an external force reference value) with respect to the magnitude of the external force included in the external force information. The external force that the flexible tube 35 receives from the large intestine wall and that is calculated by the external force calculator 83 in the above manner may be considered as a load that the flexible tube 35 applies to the large intestine wall. Accordingly, from the prospective of security, a maximum value of the magnitude of the external force is a maximum value of the load of the flexible tube 35 against the large intestine wall. Therefore, the external force reference value is, for example, a reference value for preventing the flexible tube 35 from unintentionally applying an excessive load to the large intestine wall, and for preventing pain to be caused to a patient. That is, the external force reference value is a maximum value of a load that the flexible tube 35 applies to a wall portion. The external force reference value is a value that is in common with respect to each segment 37.

The setting device 87 is connected to the storage 85, and sets the external force reference value and inputs the set external force reference value to the storage 85. The setting device 87 is operated by the operator of the insertion apparatus 10. The setting device 87 sets a desired external force reference value in accordance with, for example, a doctor, which is the operator, or a patient, which is the insertion target body, or both. The setting device 87 is, for example, general equipment for input, which, for example, is a touch panel, a keyboard, and a pointing device such as a mouse. The setting device 87 may also be omitted, and the storage 85 may have stored in advance a preset external force reference value.

When the external force information of each segment 37 is input to the external force comparator 89 from the external force calculator 83, the external force comparator 89 accesses the storage 85 and reads out the external force reference value. The readout timing may be appropriately adjusted. The external force comparator 89 compares the magnitude of the external force included in the external force information with the external force reference value stored in the storage 85, and outputs the comparison result to the stiffness controller 91. That is, the external force comparator 89 compares the magnitude of the external force in each segment 37 with the external force reference value stored in the storage 85, and outputs the comparison result in each segment 37 to the stiffness controller 91.

In accordance with the shape information calculated by the shape calculator 81, the stiffness controller 91 calculates an insertion-adequate bending stiffness that is a bending stiffness suitable for insertion of the flexible tube 35. The stiffness controller 91 calculates the insertion-adequate bending stiffness of each segment 37. The insertion-adequate bending stiffness refers to a bending stiffness that provides, to each segment 37 through the variable stiffness portion 60, a stiffness distribution suitable for insertion of the flexible tube 35 in accordance with the shape information. The insertion-adequate bending stiffness also refers to a bending stiffness that provides the stiffness distribution to the flexible tube 35 through the segment 37. In the following, an example of calculating the insertion-adequate bending stiffness for one segment 37 will be briefly explained.

For example, suppose the segments 37 receive external force from, for example, a curved portion of the large intestine. The stiffness controller 91 specifies a segment that becomes a starting point (hereinafter referred to as a starting-point segment) based on the shape information calculated by the shape calculator 81. The starting-point segment is, for example, a segment 37 that has the largest bending angle among the segments 37 that has received the external force. In other words, the starting-point segment is a segment that has received the largest external force among the segments, and is a segment that applies the largest load to the large intestine wall among the segments. Here, the segments 37 that are arranged on the proximal end side of the insertion section 30 with respect to the starting-point segment, and are continuously arranged with respect to each other, are referred to as control segments. For example, the stiffness controller 91 reduces the bending stiffness of each control segment as desired through the corresponding variable stiffness portion 60. Here, for example, the stiffness controller 91 reduces the bending stiffness of each control segment as desired so that the bending angle becomes smaller than a preset threshold value. The stiffness controller 91 may, for example, reduce the bending stiffness of each control segment lower than the bending stiffness of the other segments 37. By doing so, the bending quantity of each control segment increases, and the entirety of the insertion section 30 becomes obtuse. That is, the flexible tube 35 will obtusely come in contact with the large intestine wall of the curved portion, and the external force that the flexible tube 35 receives from the large intestine wall becomes small. Furthermore, when the bending stiffness of each control segment decreases, in some cases, the starting-point segment may be separated from the large intestine wall. Accordingly, even if an insertion force quantity for inserting the insertion section 30 towards a deep part is added to the insertion section 30, the insertion force quantity would not be converted to a force that pushes up the large intestine wall, and would be utilized as a driving force to drive the distal end of the insertion section 30 towards the deep part. Therefore, the insertion section 30 easily passes through the curved portion of the large intestine. In consideration of the above, the insertion-adequate bending stiffness is a bending stiffness capable of improving insertability, and will be a bending stiffness that is lower than a bending stiffness of when the flexible tube 35 receives an external force. The insertion-adequate bending stiffness may be a bending stiffness that is lower than the bending stiffness of when the shape information is input to the stiffness controller 91. The control segments may be continuous to the starting-point segment, or separated from the starting-point segment by a predetermined number of segments 37. The control segment may correspond to all of the segments including the starting-point segment.

When the comparison result of the external force comparator 89 indicates that the magnitude of the external force has exceeded the external force reference value, the stiffness controller 91 calculates an external force-adequate bending stiffness in which the magnitude of the external force is reduced to smaller than the external force reference value and that has an adequate bending stiffness with respect to the external force.

Figure 3:
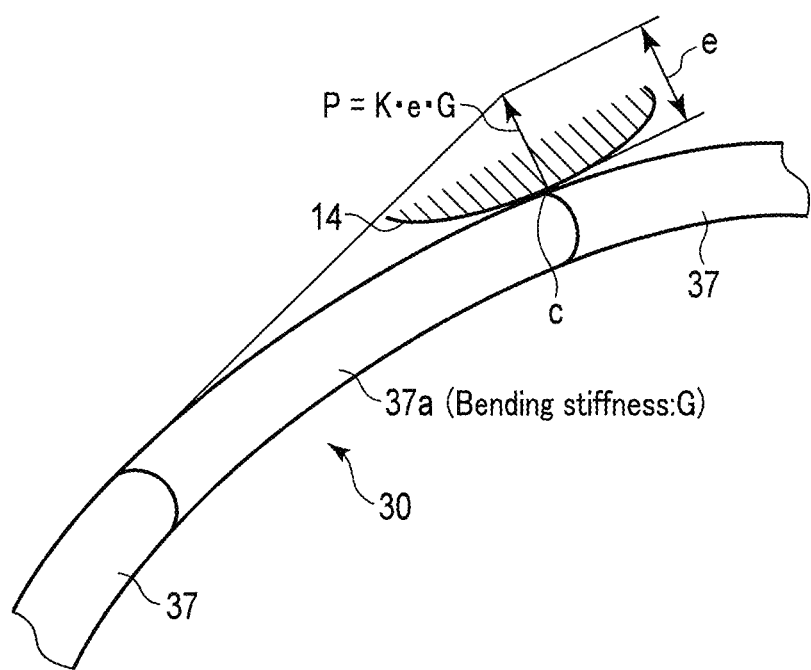
FIG. 3 is a diagram explaining a relationship between a bending stiffness with a certain magnitude at a certain segment and a magnitude of an external force that the segment receives from a large intestine wall.

Here, with reference to FIG. 3, using a segment 37a in the insertion section 30, the relationship between a bending stiffness G of the segment 37a and a magnitude P of an external force that the segment 37a receives from a large intestine wall 14 will be explained. The bending stiffness G is assumed to have a predetermined magnitude.

The segment 37a with the bending stiffness G is assumed to have come in contact with the large intestine wall 14 and to have undergone bending deformation by a displacement quantity e. In such case, the external force that the segment 37a receives from the large intestine wall 14 at a contact point C between the segment 37a and the large intestine wall 14 is a load that the segment 37a applies to the large intestine wall 14. The magnitude P of the external force is the magnitude of the load, and is expressed by the following equation (1).

$$P = K \cdot e \cdot G \qquad \text{Equation (1)}$$

Here, "K" is a constant number.

In the case where the magnitude P of the external force exceeds an external force reference value P1, the stiffness controller 91 needs to reduce the bending stiffness G so that the magnitude P of the external force becomes smaller than the external force reference value P1. The external force (load) in this case is an external force (load) that still would not cause pain to the patient, but may cause pain if the external force (load) is somewhat larger. When a reduction quantity of the bending stiffness is defined as ΔG, and is substituted in equation (1), the reduction quantity ΔP of the magnitude P of an external force is expressed by the following equation (2).

$$\Delta P = K \cdot e \cdot \Delta G \quad \text{Equation (2)}$$

The relationship between equations (1) and (2) and the magnitude P of the external force and the external force reference value P1 is expressed by the following equation (3).

$$P - \Delta P = K \cdot e(G - \Delta G) < P1 \quad \text{Equation (3)}$$

"(G−ΔG)" is a value of the external force-adequate bending stiffness.

Accordingly, the stiffness controller 91 calculates the external force-adequate bending stiffness for the segment 37a based on equation (3). The stiffness controller 91 calculates the external force-adequate bending stiffness for each segment 37. The external force-adequate bending stiffness refers to a bending stiffness that provides, to each segment 37 through the variable stiffness portion 60, a stiffness distribution in which the external force is reduced to smaller than the external force reference value. The insertion and external force-adequate bending stiffness refers to a bending stiffness that provides the stiffness distribution to the flexible tube 35 through the segment 37.

Based on the insertion-adequate bending stiffness and the external force-adequate bending stiffness, the stiffness controller 91 calculates the insertion and external force-adequate bending stiffness that is a bending stiffness suitable for insertion of the flexible tube 35 in accordance with the shape information and that is a bending stiffness in which the magnitude of the external force becomes smaller than the external force reference value. The stiffness controller 91 controls the bending stiffness to be the insertion and external force-adequate bending stiffness through the variable stiffness portion 60. The stiffness controller 91 calculates the insertion and external force-adequate bending stiffness for each segment 37, and controls the bending stiffness for each segment 37 to be the insertion and external force-adequate bending stiffness. The insertion and external force-adequate bending stiffness refers to a bending stiffness that provides, to each segment 37 through the variable stiffness portion 60, a stiffness distribution in which the magnitude of the external force does not exceed the external force reference value, and that is suitable for insertion of the flexible tube 35 in accordance with the shape information in a range that does not exceed the external force reference value. The insertion and external force-adequate bending stiffness is a bending stiffness that provides the stiffness distribution to the flexible tube 35 through the segments 37.

Generally, the external force-adequate bending stiffness is considered to be a bending stiffness that is lower than the insertion-adequate bending stiffness value. Accordingly, the stiffness controller 91 may adopt the external force-adequate bending stiffness in priority to the insertion-adequate bending stiffness as the insertion and external force-adequate bending stiffness without being influenced by the external force and the external force reference value.

In the above manner, the stiffness controller 91 controls a change of the bending stiffness implemented by the variable stiffness portion 60 based on the calculated insertion-adequate bending stiffness and the calculated external force-adequate bending stiffness.

In the following, the operation of the insertion apparatus 10 will be explained. The following is an explanation for a segment 37; however, the same operation will be implemented for each segment 37.

Suppose the insertion section 30 inserted in the intestine tract 12 bends in accordance with the shape of the intestine tract 12. The state information of the flexible tube 35 is detected by the state detection sensor 70, and the state detection sensor 70 outputs the state information to the shape calculator 81 and the external force calculator 83. The shape calculator 81 calculates the shape information based on the state information, and the external force calculator 83 calculates the external force information based on the state information. The shape calculator 81 outputs the shape information to the stiffness controller 91, and the external force calculator 83 outputs the external force information to the external force comparator 89.

The external force comparator 89 accesses the storage 85 and reads out the external force reference value. The external force comparator 89 compares the magnitude of the external force included in the external force information with the external force reference value, and outputs the comparison result to the stiffness controller 91. Here, suppose the segment 37 abuts the large intestine wall 14 at the curved portion, and the magnitude of the external force that the flexible tube 35 receives from the large intestine wall 14 exceeds the external force reference value. As mentioned above, the external force is a load that the flexible tube 35 applies to the large intestine wall 14.

In this state, suppose the bending stiffness of the flexible tube 35 is not controlled yet. In this state, when the insertion force quantity is added to the insertion section 30, the insertion force quantity will be converted to a force that pushes up the large intestine wall 14, and would hardly cause any driving force to be generated to drive the distal end of the insertion section 30 towards the deep part. Therefore, the flexible tube 35 would not pass through the curved portion, and the insertability of the flexible tube 35 would not be improved. Furthermore, the flexible tube 35 that pushes up the large intestine wall 14 by the insertion force quantity would unintentionally apply an excessive load to the large intestine wall 14, which would cause pain to the patient.

However, in the present embodiment, the stiffness controller 91 calculates the insertion-adequate bending stiffness in accordance with the shape information, and calculates the external force-adequate bending stiffness when the magnitude of the external force exceeds the external force reference value. The stiffness controller 91 calculates the insertion and external force-adequate bending stiffness based on the insertion-adequate bending stiffness and the external force-adequate bending stiffness. The stiffness controller 91 drives the variable stiffness portion 60 so that the bending stiffness of the segment 37 becomes the insertion and external force-adequate bending stiffness. When the variable stiffness portion 60 changes the stiffness of the variable stiffness portion 60, the bending stiffness of the segment 37 is changed to the insertion and external force-adequate bending stiffness. The insertion and external force-adequate bending stiffness not only deals with the improvement of insertability, but also deals with the magnitude of the load that the flexible tube 35 applied to the large intestine wall 14.

Accordingly, even if the insertion force quantity is added to the insertion section 30, the insertion force quantity would not be converted to a force that pushes up the large intestine wall 14, and would instead be utilized as the driving force. Therefore, the flexible tube 35 passes through the curved portion, and the insertability of the insertion section 30, which includes the flexible tube 35, is improved. Furthermore, the large intestine wall 14 would not be pushed up by the insertion force quantity, and the external force would be reduced to smaller than the external force reference value. Accordingly, the flexible tube 35 would not unintentionally apply an excessive load to the large intestine wall 14; therefore, would cause the patient less pain.

For example, in the case where the magnitude of the external force is larger than the external force reference value, the stiffness controller 91 may regard the external force-adequate bending stiffness as the insertion and external force-adequate bending stiffness, and may control the bending stiffness to be the external force-adequate bending stiffness (insertion and external force-adequate bending stiffness). Specifically, for each segment 37 of which the magnitude of the external force is larger than the external force reference value, the stiffness controller 91 controls the bending stiffness to be the external force-adequate bending stiffness (insertion and external force-adequate bending stiffness).

Furthermore, in the case where, for example, the magnitude of the external force is smaller than the external force reference value, the stiffness controller 91 may regard the insertion-adequate bending stiffness as the insertion and external force-adequate bending stiffness, and control the bending stiffness to be the insertion-adequate bending stiffness (insertion and external force-adequate bending stiffness). Specifically, for each segment 37 of which the magnitude of the external force is smaller than the external force reference value, the stiffness controller 91 controls the bending stiffness to be the insertion-adequate bending stiffness (insertion and external force-adequate bending stiffness).

Accordingly, the stiffness controller 91 may regard one of the insertion-adequate bending stiffness and the external force-adequate bending stiffness as the insertion and external force-adequate bending stiffness in accordance with the magnitude of the external force, and may switch the bending stiffness to the insertion and external force-adequate bending stiffness.

In the present embodiment, the stiffness controller 91 calculates the insertion-adequate bending stiffness and the external force-adequate bending stiffness, and controls the change of the bending stiffness based on the insertion-adequate bending stiffness and the external force-adequate bending stiffness. Specifically, the stiffness controller 91 calculates the insertion and external force-adequate bending stiffness based on the insertion-adequate bending stiffness and the external force-adequate bending stiffness, and changes the bending stiffness to the insertion and external force-adequate bending stiffness. The insertion and external force-adequate bending stiffness not only deals with the improvement of insertability, but also deals with the magnitude of the load that the flexible tube 35 applies to the large intestine wall 14. Accordingly, in the present embodiment, the insertability of the insertion section 30, which includes the flexible tube 35, to a deep part of the tract section can be improved, and the load applied to the insertion target body can be reduced without an excessive load being unintentionally applied to the wall portion of the tract section. In the present embodiment, for example, the insertability of the insertion section 30 to a deep part of the large intestine can be improved, and less pain will be caused to the patient without an excessive load being unintentionally applied to the large intestine wall 14. Furthermore, according to the present embodiment, a stiffness distribution in which the magnitude of the external force does not exceed the external force reference value and that, in a range that does not exceed the external force reference value, is suitable for insertion of the flexible tube 35 in accordance with the shape information, can be obtained. Accordingly, a safe and simple insertion operation can be implemented, and a safe and easy-to-use endoscope 20 can be provided.

In the present embodiment, in each segment 37, the bending stiffness is controlled to be the insertion and external force-adequate bending stiffness. Accordingly, in the present embodiment, the bending stiffness of the flexible tube 35 can be finely controlled.

In the present embodiment, the storage 85 stores the external force reference value. Accordingly, in the present embodiment, the stiffness controller 91 is capable of rapidly calculating the external force-adequate bending stiffness, and rapidly controlling the bending stiffness of the flexible tube 35.

The external force reference value is a maximum value of the load of the flexible tube 35 with respect to the large intestine wall 14. Accordingly, in the present embodiment, an excessive load can reliably be prevented from being unintentionally applied to the large intestine wall 14; which would cause less pain to the patient.

In the present embodiment, a desired external force reference value can be set in accordance with a doctor, a patient, etc. by the setting device 87 that sets the external force reference value. Accordingly, utilization efficiency of the insertion apparatus 10 can be improved.

In the present embodiment, the external force-adequate bending stiffness is a bending stiffness that is lower than the insertion-adequate bending stiffness. Accordingly, the stiffness controller 91 may adopt the external force-adequate bending stiffness in priority to the insertion-adequate bending stiffness as the insertion and external force-adequate bending stiffness. In the present embodiment, the insertability of the insertion section 30 to a deep part of the tract section can assuredly be improved, and the load applied to the insertion target body can be reduced without an excessive load being unintentionally applied to the wall portion of the tract section. Furthermore, the external force-adequate bending stiffness has a bending stiffness that is smaller than and is approximated to the insertion-adequate bending stiffness. In such case, the external force-adequate bending stiffness may also be considered as having a bending stiffness in which the magnitude of the external force is reduced to smaller than the external force reference value, and that is not only adequate for the external force, but is also suitable for insertion of the flexible tube 35. Accordingly, the insertability of the insertion section 30 to a deep part of the tract section can be improved, and the load applied to the insertion target body can be reduced without an excessive load being unintentionally applied to the wall portion of the tract section.

In the present embodiment, in the case where the magnitude of the external force is larger than the external force reference value, the stiffness controller 91 may regard the external force-adequate bending stiffness as the insertion and external force-adequate bending stiffness, and may control the bending stiffness to be the external force-adequate bending stiffness (insertion and external force-adequate bending stiffness). In the present embodiment, the load applied to the insertion target body can reliably be reduced without an excessive load being unintentionally applied to the wall portion of the tract section at all.

Furthermore, in the case where, for example, the magnitude of the external force is smaller than the external force reference value, the stiffness controller 91 may regard the insertion-adequate bending stiffness as the insertion and external force-adequate bending stiffness, and control the bending stiffness to be the insertion-adequate bending stiffness (insertion and external force-adequate bending stiffness). The present embodiment is able to immediately provide improvement in the insertability of the insertion section 30.

The present invention is not limited to the exact embodiment described above; the invention can be embodied by modifying the structural elements without departing from the gist of the invention when being implemented. In addition, various inventions can be made by properly combining the structural elements disclosed in the above embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
   a flexible tube that is to be inserted in an insertion target body;
   a variable stiffness portion that changes a bending stiffness of the flexible tube;
   a state detection sensor that detects state information including information of magnitude of bending of the flexible tube;
   a shape calculator that calculates shape information regarding a shape of the flexible tube based on the state information;
   an external force calculator that calculates external force information including magnitude of an external force received by the flexible tube based on the state information; and
   a stiffness controller that controls the variable stiffness portion in accordance with the shape information so that the magnitude of the external force received by the flexible tube becomes smaller than a predetermined external force reference value.

2. The flexible tube insertion apparatus according to claim 1, further comprising an external force comparator that compares the magnitude of the external force and the external force reference value, wherein
   the stiffness controller calculates an insertion-adequate bending stiffness that is a bending stiffness suitable for insertion of the flexible tube in accordance with the shape information, and an external force-adequate bending stiffness that is a bending stiffness in which the magnitude of the external force is reduce to smaller than the external force reference value and that is adequate with respect to the external force, and controls a change of the bending stiffness implemented by the variable stiffness portion based on the calculated insertion-adequate bending stiffness and the calculated external force-adequate bending stiffness.

3. The flexible tube insertion apparatus according to claim 2, wherein, based on the insertion-adequate bending stiffness and the external force-adequate bending stiffness, the stiffness controller calculates an insertion and external force-adequate bending stiffness that is a bending stiffness that is suitable for insertion of the flexible tube in accordance with the shape information and a bending stiffness in which the magnitude of the external force becomes smaller than the external force reference value, and controls the bending stiffness to become the insertion and external force-adequate bending stiffness.

4. The flexible tube insertion apparatus according to claim 3, wherein the flexible tube is segmented into segments that are aligned in a row along a central axis of the flexible tube,
   the variable stiffness portion varies the bending stiffness by units of segments,
   the shape calculator calculates the shape information of each segment based on the state information,
   the external force calculator detects the external force in each segment based on the state information,
   the external force comparator compares the magnitude of the external force in each segment and the external force reference value, and
   the stiffness controller calculates the insertion and external force-adequate bending stiffness in each segment, and controls the bending stiffness to become the insertion and external force-adequate bending stiffness in each segment.

5. The flexible tube insertion apparatus according to claim 3, comprising a storage that stores the external force reference value.

6. The flexible tube insertion apparatus according to claim 5, comprising a setting device that sets the external force reference value, and inputs the set external force reference value to the storage.

7. The flexible tube insertion apparatus according to claim 3, wherein in a case where the magnitude of the external force is smaller than the external force reference value, the stiffness controller regards the insertion-adequate bending stiffness as the insertion and external force-adequate bending stiffness, and controls the bending stiffness to become the insertion-adequate bending stiffness, and
   in a case where the magnitude of the external force is larger than the external force reference value, the stiffness controller regards the external force-adequate bending stiffness as the insertion and external force-adequate bending stiffness, and controls the bending stiffness to become the external force-adequate bending stiffness.

* * * * *